US007387121B2

(12) United States Patent
Harvey

(10) Patent No.: US 7,387,121 B2
(45) Date of Patent: Jun. 17, 2008

(54) VALVE FOR AEROSOL CONTAINER

(75) Inventor: Stephen James Harvey, Ware (GB)

(73) Assignee: SmithKline Beechem Corporation, Philadelphia, PA (US)

( * ) Notice: Subject to any disclaimer, the term of this patent is extended or adjusted under 35 U.S.C. 154(b) by 787 days.

(21) Appl. No.: 10/312,027

(22) PCT Filed: Jul. 2, 2001

(86) PCT No.: PCT/GB01/02885

§ 371 (c)(1),
(2), (4) Date: Dec. 19, 2002

(87) PCT Pub. No.: WO02/02167

PCT Pub. Date: Jan. 10, 2002

(65) Prior Publication Data
US 2003/0106550 A1    Jun. 12, 2003

(30) Foreign Application Priority Data
Jul. 1, 2000 (GB) .................................. 0016123.2

(51) Int. Cl.
*A61M 16/00* (2006.01)
*A62B 9/02* (2006.01)

(52) U.S. Cl. .............................. 128/203.15; 128/205.24

(58) Field of Classification Search ...............................
128/200.14–200.17, 200.21–200.23, 203.12,
128/203.13, 203.15, 203.19, 205.19, 205.22,
128/205.24; 424/45, 46, 400; 239/333,
239/349, 533.15, 571, 583, 321, 337; 604/24,
604/37, 38, 45; 137/145, 533.17, 533.23,
137/467; 251/94, 903, 82, 83, 73; 222/383.1,
222/385, 401, 402.1, 1, 402.2, 402.23, 162,
222/402.13
See application file for complete search history.

(56) References Cited

U.S. PATENT DOCUMENTS

| | | | |
|---|---|---|---|
| 3,082,959 A * | 3/1963 | Boris | 239/329 |
| 3,360,168 A * | 12/1967 | Bret | 222/335 |
| 3,756,465 A | 9/1973 | Meshberg | |
| 3,789,843 A * | 2/1974 | Armstrong et al. | 128/200.23 |
| 4,030,644 A | 6/1977 | Creighton | |
| 4,260,080 A | 4/1981 | Gailitis | |
| 4,534,345 A * | 8/1985 | Wetterlin | 128/203.15 |
| 4,573,611 A | 3/1986 | O'Connor | |
| 4,576,157 A | 3/1986 | Raghuprasad | |
| 4,813,575 A | 3/1989 | O'Connor | |
| 4,896,832 A | 1/1990 | Howlett | |
| 5,025,962 A | 6/1991 | Renfro | |
| 5,125,546 A * | 6/1992 | Dunne et al. | 222/394 |
| 5,261,538 A | 11/1993 | Evans et al. | |
| 5,295,502 A | 3/1994 | Lane | |
| 5,345,980 A | 9/1994 | Burt et al. | |
| 5,400,920 A * | 3/1995 | Barnhart | 222/1 |
| 5,450,336 A * | 9/1995 | Rubsamen et al. | 702/104 |
| 5,772,085 A | 6/1998 | Bryant et al. | |
| 5,791,524 A | 8/1998 | Demarest | |
| 6,003,737 A | 12/1999 | Mascitelli | |
| 6,003,739 A | 12/1999 | Bartlett et al. | |
| 6,290,104 B1 | 9/2001 | Bougamont et al. | |
| 6,871,799 B2 * | 3/2005 | Tsutsui | 239/337 |
| 6,889,687 B1 * | 5/2005 | Olsson | 128/200.14 |
| 7,104,470 B2 * | 9/2006 | Jaeger et al. | 239/333 |
| 7,185,648 B1 * | 3/2007 | Rand | 128/200.23 |
| 2002/0020408 A1 * | 2/2002 | Knauer | 128/200.14 |

FOREIGN PATENT DOCUMENTS

* cited by examiner

FOREIGN PATENT DOCUMENTS

EP    0870699    10/1998
WO    WO96/28367    9/1996

*Primary Examiner*—Justine R. Yu
*Assistant Examiner*—Shumaya B Ali
(74) *Attorney, Agent, or Firm*—J. Michael Strickland

(57) ABSTRACT

There is provided a propellant-operable self-activating and self-returning metering valve for an aerosol container for dispensing a formulation comprising a substance in a fluid propellant contained therein. There is also provided a canister for use in a metered dose inhaler having the valve thereon.

46 Claims, 3 Drawing Sheets

VALVE FOR AEROSOL CONTAINER

The present invention relates to valves for use in aerosol containers. More especially, the invention relates to a valve having a propellant driven self-returning mechanism.

Drugs for treating respiratory and nasal disorders are frequently administered in aerosol formulations through the mouth or nose. One widely used method for dispensing such aerosol drug formulations involves formulating the drug as a suspension or a solution in a liquefied gas propellant. The suspension/solution is stored in a sealed canister capable of withstanding the pressure required to maintain the propellant as a liquid. The suspension/solution is dispersed by activation of a dose-metering valve affixed to the canister.

A metering valve generally comprises a metering chamber that is of a set volume and is designed to administer per actuation an accurate predetermined dose of medicament. As the suspension is forced from the canister through the dose-metering valve by the high vapour pressure of the propellant, the propellant rapidly vapourizes leaving a fast moving cloud of very fine particles of the drug formulation. This cloud of particles is directed into the nose or mouth of the patient by a channeling device such as a cylinder or open-ended cone. Concurrently with the activation of the aerosol dose-metering valve, the patient inhales the drug particles into the lungs or nasal cavity. Systems of dispensing drugs in this way are known as "metered dose inhalers" (MDI's). See Peter Byron, Respiratory Drug Delivery, CRC Press, Boca Raton, Fla. (1990) for a general background on this form of therapy.

Patients often rely on medication delivered by MDI's for rapid treatment of respiratory disorders that are debilitating and in some cases even life threatening. Therefore, it is essential that the prescribed dose of aerosol medication delivered to the patient consistently meet the specifications claimed by the manufacturer and comply with the requirements of the FDA and other regulatory authorities. That is, every dose delivered from the canister must be the same within close tolerances.

Conventional metering valves for use with pressurized containers comprise a valve stem coaxially slidable within a valve member defining an annular metering chamber, and outer and inner seals operative between the respective outer and inner ends of the valve stem and the valve member to seal the metering chamber therebetween. The valve stem is hollow whereby in a non-dispensing position of the valve stem, the metering chamber is connected to the container and charged with product therefrom. The valve stem is movable to a dispensing position wherein the metering chamber is isolated from the container and vented to the atmosphere for the discharge of product. At rest, the valve can be biased towards the non-dispensing or dispensing position by, for example, a spring, or by the internal pressure exerted by the propellant composition.

However, all conventional propellant-driven dispensers require manual activation and resetting prior to each dose discharge. Therefore, it is an object of the present invention to provide a valve for use in an aerosol container that uses a propellant-driven mechanism to activate and automatically reset the valve so that it is primed, ready to dispense the next dose.

Accordingly in one aspect, the invention provides a propellant-operable self-activating and self-returning metering valve for an aerosol container for dispensing a formulation comprising a substance in a fluid propellant contained therein.

Preferably, the valve comprises latching means.

In one embodiment, the valve may be breath-operable and the latching means may be a breath activation lock.

Alternatively or in addition, the latching means may comprise a mechanical manual-activation lock and/or an electronic activation lock and/or an electrically-operable activation lock.

Most preferably, the valve comprises a valve member movable within a valve body, the valve member having a first reaction surface and a second reaction surface, wherein pressure exerted by the propellant on the first reaction surface drives the valve member from a first position to a second position within the valve body and pressure exerted by the propellant on the second reaction surface returns the valve member to the first position.

Typically, movement of the valve member between the first and second positions switches the valve between a first dispensing sequence wherein one dose of formulation is discharged from the valve, and a second dispensing sequence wherein a second dose of formulation is dispensed from the valve.

The valve member and the valve body may define a first metering chamber having a first metering volume, and a second metering chamber having a second metering volume. The first metering volume may be equal to the second metering volume Preferably, the valve body has a first priming inlet allowing free-flow of formulation into the first metering chamber to form the first metering volume, and a second priming inlet allowing free-flow of formulation into the second metering chamber to form the second metering volume.

In one embodiment the valve member is a valve stem and pressure exerted by the propellant elicits a reciprocal piston movement of the stem within the valve body to switch the valve between the first and the second dispensing sequences.

The valve stem and the valve body may define annular first and second metering chambers.

The first reaction surface may take the form of a first piston head surface and the second reaction surface may take the form of a second piston head surface.

The valve of the present invention uses the pressure exerted by the propellant in the canister to drive the valve member in one direction and then return the valve to its original position. In one embodiment, one metering chamber captures a dose as the valve member travels in one direction, and the other metering chamber captures a dose as the valve member reverses its direction of travel. Therefore, in the embodiment where the valve member is a valve stem, downward piston action discharges one dose of formulation and upward piston action discharges another dose of formulation.

Typically, the cross-sectional area of the second reaction surface is greater than the cross-sectional area of the first reaction surface.

In another embodiment, the valve member is a rotating disk and pressure exerted by the propellant elicits a clockwise and anti-clockwise rotation of the disk within the valve body to switch the valve between the first and the second dispensing sequences.

Alternatively, the valve member may be a rotating disk and pressure exerted by the propellant elicits a clockwise or anti-clockwise rotation of the disk within the valve body to drive the valve between the first and the second dispensing sequences.

Preferably, the rotating disk and the valve body define wedge-shaped annular first and second metering chambers.

Typically, each of the first and second metering chambers have two opposing faces defined by the disk, a leading face and a secondary face, the leading face having a greater cross-sectional area than the secondary face, such that the first leading face is the first reaction surface and the second leading face is the second reaction surface.

The first and the second reaction surfaces may be equal in cross-sectional area.

Preferably, the valve member is restrained by latching means at one or more of the following stages:
(i) during the first dispensing sequence; and/or
(ii) during the second dispensing sequence.

The valve may be latched at the position where the first and/or second metering chamber is in free-flow communication with the formulation in the aerosol container.

Breath-actuable or breath-assisted inhalation devices have been developed to address the needs of patients having poor co-ordination skills and/or unreliable breath capability. Such devices typically have a breath trigger mechanism that triggers release of medicament in response to the inward breath of a patient.

Preferably, the breath-operable valve comprises a monitor for monitoring the breath cycle of a patient, for example, one or more vanes or sails that are movable in response to airflow.

Preferably, the monitor comprises one or more sensors for sensing:
(i) the pressure profile associated with a breath cycle (e.g. a pressure transducer); and/or
(ii) the airflow profile associated with a breath cycle (sprung vane sensors and/or anemometers); and/or
(iii) the temperature profile associated with a breath cycle; and/or
(iv) the moisture profile associated with a breath cycle; and/or
(v) the chemical profile associated with a breath cycle.

Typically, the monitor provides a signal for dispensing the formulation at a trigger point. The trigger point may coincide with the point at which a patient's lungs are empty.

The monitor may comprise an electronic information processor that optionally has a predictive algorithm for predicting the optimal trigger point.

Preferably, inner and/or outer seals are operative between the inner and/or outer ends respectively, of the valve member and valve body to seal the first and/or second metering chamber therebetween.

In one embodiment, the second metering chamber communicates with the formulation in the aerosol container via at least one return channel through the valve body.

Preferably, the valve member comprises at least one recess or aperture such that second metering chamber communicates with the or each return channel via the or each recess.

The valve preferably comprises outlet means that direct the aerosol formulation to either an outlet nozzle or orifice, or to a different area of the valve such that the formulation exits the valve via an additional discharge passage.

Typically, the valve of the present invention is for use in a metered dose inhaler.

As used herein, the term "metered dose inhaler" or "MDI" means a unit comprising a canister, a crimped cap covering the mouth of the canister, a drug metering valve situated in the cap, a metering chamber and a suitable channelling device into which the canister is fitted. The term "drug metering valve" or "MDI valve" refers to a valve and its associated mechanisms that deliver a predetermined amount of drug formulation from an MDI upon each activation. The channelling device may comprise, for example, an actuating device for the valve and a cylindrical or cone-like passage through which medicament may be delivered from the filled MDI can via the MDI valve to the nose or mouth of a patient, e.g. a mouthpiece actuator. The relation of the parts of a typical MDI is illustrated in U.S. Pat. No. 5,261,538.

In one embodiment, the valve contains a formulation comprising a substance in a fluid propellant.

In another embodiment, the invention provides a canister for use in a metered dose inhaler having thereon a valve as defined hereinabove.

Typically, the canister contains a pharmaceutical aerosol formulation comprising a medicament and a fluorocarbon propellant.

Aerosol formulations that are generally used comprise a solution/suspension of medicament, one or more liquid propellants, optionally with co-propellants and optionally an adjuvant or a surfactant, though the invention may be applicable to the dispensing of any aerosol formulation.

Preferably, the propellant is liquefied HFA 134a, 227 or a mixture thereof.

Typically, the propellant is substantially free of adjuvants.

The medicament may be selected from fluticasone propionate, salbutamol, beclomethasone dipropionate, salmeterol, pharmaceutically acceptable salts, solvates or esters thereof and mixtures thereof.

In yet another embodiment, the invention provides a metered dose inhaler comprising a valve as defined hereinabove, and/or a canister as defined hereinabove.

In one embodiment, the metered dose inhaler comprises a breath-activation device.

Typically, the breath-activation device comprises a monitor for monitoring the breath cycle of a patient.

Preferably, the monitor comprises one or more sensors for sensing:
(i) the pressure profile associated with a breath cycle (e.g. a pressure transducer); and/or
(ii) the airflow profile associated with a breath cycle (sprung vane sensors and/or anemometers); and/or
(iii) the temperature profile associated with a breath cycle; and/or
(iv) the moisture profile associated with a breath cycle; and/or
(v) the chemical profile associated with a breath cycle.

The monitor may provide a signal for dispensing the formulation at a trigger point. The monitor may comprise an electronic information processor that has a predictive algorithm for predicting the optimal trigger point.

In still another aspect, the invention provides a method for dispensing a formulation comprising a substance in a fluid propellant from a metered dose inhaler, such that after dispensing one dose the inhaler is automatically primed for further dose release, comprising the use of a valve as defined hereinabove and/or the use of a canister as defined hereinabove.

In yet another aspect, the invention provides a method for dispensing a formulation comprising a substance in a fluid propellant from a metered dose inhaler, such that after dispensing one dose the inhaler is automatically primed for further dose release, the method comprising a propellant-driven operative cycle wherein pressure exerted by the propellant on a first reaction surface drives a valve member from a first position to a second position and pressure exerted by the propellant on a second reaction surface returns the valve member to the first position.

Typically, the propellant-driven operative cycle comprises a first dispensing sequence and a second dispensing sequence, the first dispensing sequence comprising:
(i) propellant-driven formation of a first charging position allowing free-flow of formulation into a first metering chamber;
(ii) the formation of a defined first metering volume;
(iii) a first dispensing position wherein the first metering volume is discharged to a patient;

and the second dispensing sequence comprising:
(i) a second charging position allowing free-flow of formulation into a second metering chamber;
(ii) the formation of a defined second metering volume;
(iii) a second dispensing position wherein the second metering volume is discharged to the patient;
(iv) a return to the first charging position In yet a further aspect, the invention provides the use of a valve as defined hereinabove, and/or a canister as defined hereinabove, in a metered dose inhaler.

Preferably, the invention provides the use of a valve and/or a canister and/or a metered dose inhaler as defined hereinabove, for dispensing a pharmaceutical aerosol formulation comprising a medicament and a fluorocarbon propellant.

Preferably, the pharmaceutical aerosol formulation to be dispensed is a medicament suspended in propellants selected from liquefied HFA 134a, 227 or a mixture thereof.

Typically, the propellant is substantially free of adjuvants.

The medicament maybe selected from fluticasone propionate, salbutamol, beclomethasone dipropionate, salmeterol, pharmaceutically acceptable salts, solvates or esters thereof and mixtures thereof.

The invention will now be described further with reference to the following drawings which serve to illustrate the invention but are not intended to be limiting, in which.

Figure 1:
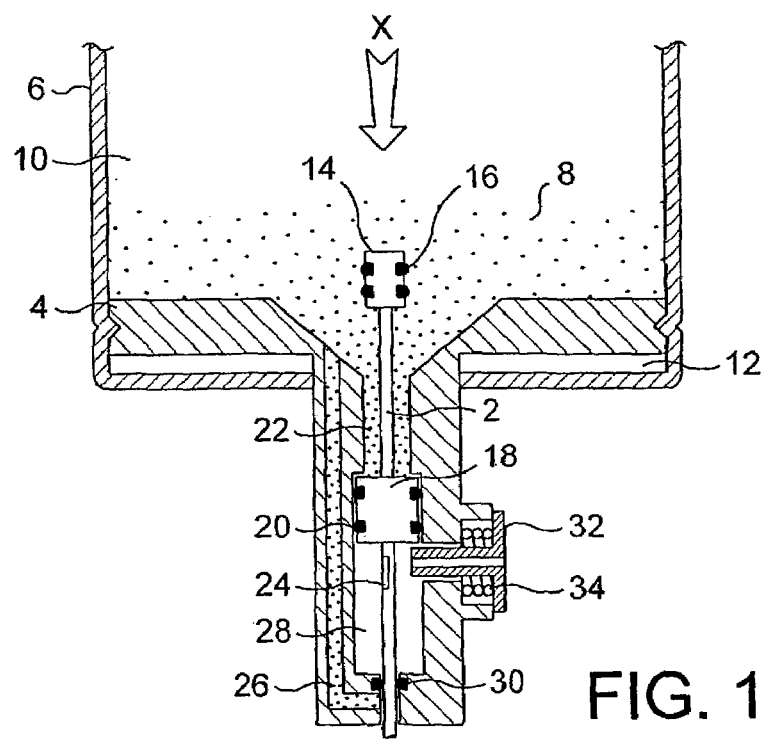
FIG. 1 illustrates a self-returning valve according to the invention having a breath activation lock, during the first dispensing sequence at the first charging position.

With reference to the figures, FIG. 1 illustrates a self-returning valve assembly in accordance with the invention having a valve stem 2 reciprocally slidable within a valve body 4. The valve assembly is inserted into the neck of a canister 6 containing a propellant-containing drug formulation 8 in a drug reservoir 10, via a sealing canister gasket 12. The valve stem 2 comprises a piston head "A" 14 having two sealing rings 16, and piston head "B" 18, also having two sealing rings 20. Defined between piston heads "A" and "B" lies a first metering chamber 22. The stem 2 further comprises a recess 24 which serves to communicate between a return channel 26 which is linked to the drug-formulation reservoir 10, and a second metering chamber 28, when the stem is inserted further into the valve body 4 (see FIG. 4).

Although the figure illustrates the second metering chamber 28 as defined by the valve stem 2 and the valve body 4, it is also contemplated that the chamber take the form of a sealed piston/cylinder. Furthermore, the valve stem 2 may be made from a one or two component moulding. Preferably, the stem 2 is manufactured as a two component moulding.

Further seals are present on the valve body 30. The valve in FIG. 1 is arrested during the first dispensing sequence by a breath activation peglock 32 having a return spring 34 so that after breath activation and drug discharge, the lock will reseal.

FIG. 1 illustaes the fist charging position during the first dispensing sequence. The pressure exerted by the drug formulation on piston head "A" 14 is such to urge the valve stem 2 through the valve body 4 (as shown by arrow X). However, the breath activation lock restrains the stem 2 such that the first metering chamber 22 is in direct communication with the drug reservoir 10.

Figure 2:
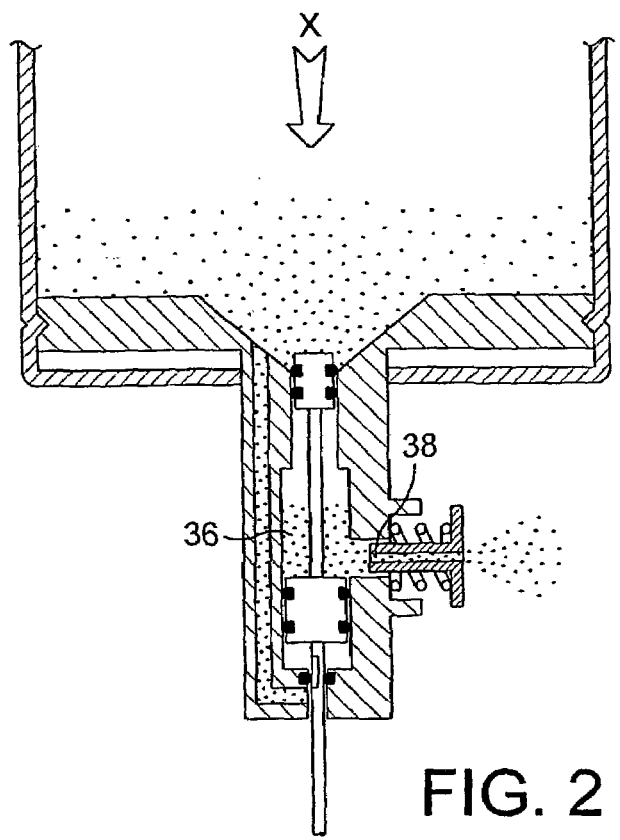
FIG. 2 illustrates the valve of FIG. 1 during the first dispensing sequence at the first dispensing position.

In FIG. 2, the breath activation lock 32 has been released and the pressure X exerted by the drug formulation is such to drive the stem 2 down into the valve body 4. A first closed metered dose volume 36 is thus captured in the first metering chamber 22 and as the continued pressure drives the piston head "B" 18 past the body opening 38 housing the activation lock, the drug is released.

Figure 3:
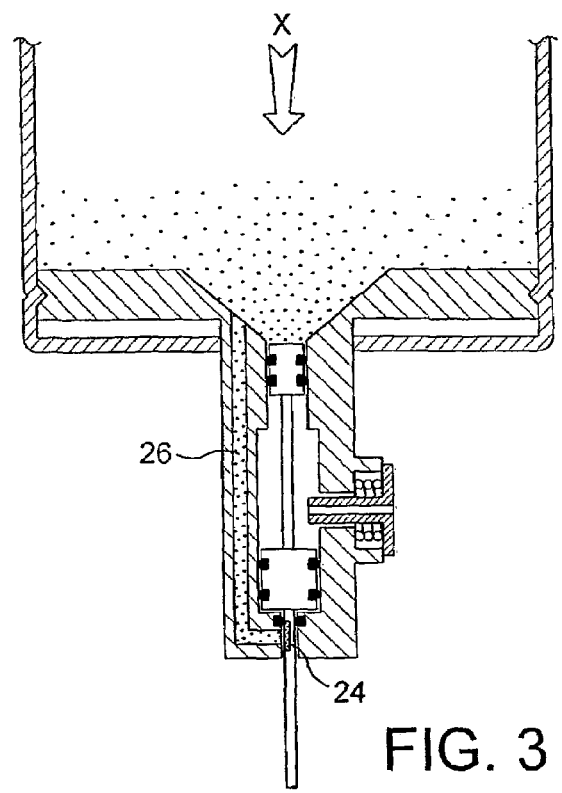
FIG. 3 illustrates the valve of FIGS. 1 and 2 during the second dispensing sequence at the second charging position.
Figure 4:
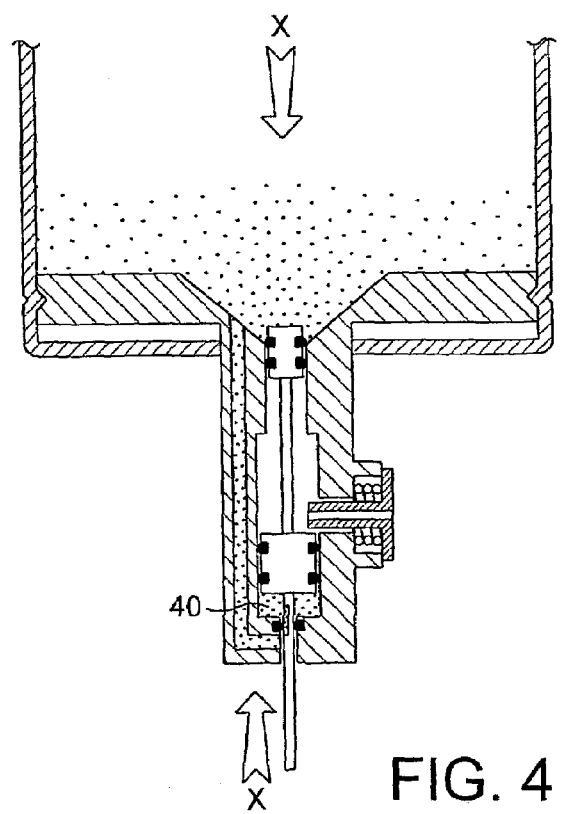
FIG. 4 illustrates the valve of FIGS. 1 to 3 during the second dispensing sequence at the closed second metering volume position.
Figure 5:
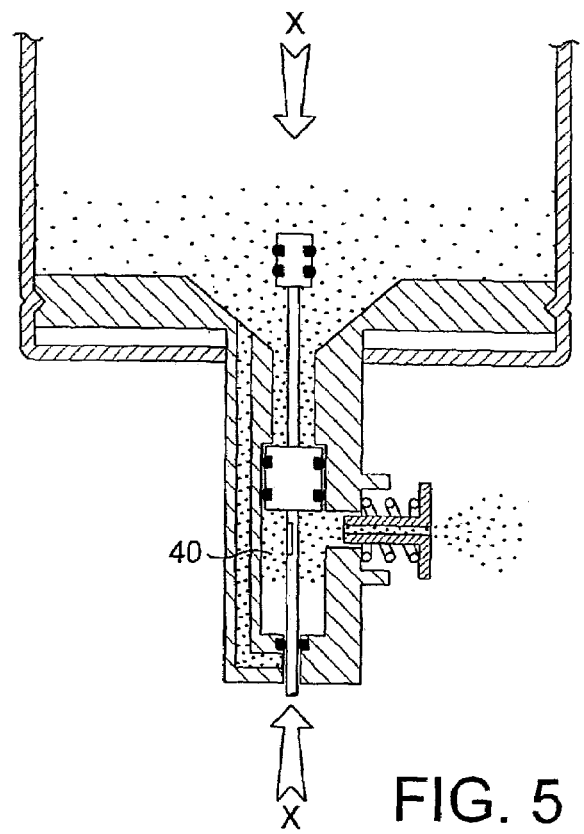
FIG. 5 illustrates the valve of FIGS. 1 to 4 during the second dispensing sequence at the second dispensing position; and, FIG. 6 illustrates an alternative embodiment of the invention in which the self-returning valve is a rotary valve.

In FIG. 3, continued pressure X exerted by the drug formulation drives the stem 2 through the valve body 4 until the recess 24 in the valve stem 2 is in direct communication with the return channel 26 leading to the drug reservoir 10. At this stage, the drug formulation 8 begins to enter the second metering chamber 28 and exert a pressure on the piston head "B" 18. There is now an equal but opposing pressure on piston head "A" 14 and on piston head "B" 18. However, the exposed surface area of piston head "B" 18 is larger than the exposed surface area of piston head "A" 14. As, the force on a surface is directly proportional to the surface area, there is a greater inward force on piston head "B" 18. Accordingly, as shown in FIG. 4, the stem 2 reverses direction of movement, moves back upwards through the valve body 4 and breaks the communicating link between the drug formulation reservoir 10 and the second metering chamber 28 via the recess 24. At this point a 5 closed second metering volume 40 exists in the second metering chamber 28. Further movement of the stem 2 through the valve body 4 is arrested by the breath activation lock 32. Further activation of the lock 32 results in the discharge of the second drug metered volume 40 (FIG. 5). Evacuation of the second metering chamber 28 returns the valve assembly to the position illustrated in FIG. 1 and the cycle is primed to start again.

Figure 6:
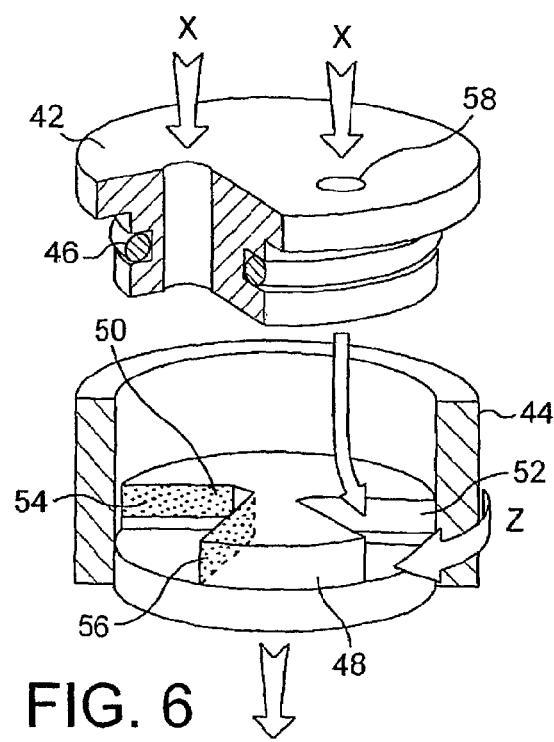

FIG. 6 illustrates another form of valve in accordance with the present invention. The valve shown is a rotary valve and comprises a valve body having a top plate 42 and a bottom plate 44. The top plate 42 has an "O"-ring seal 46 to ensure sealing contact with the bottom plate 44. The valve member takes the form of a rotating disk 48 having two wedge-shaped metering chambers 50, 52. Each wedge-shaped chamber has two opposing faces, "A", 54, and "B", 56. The top plate 42 has two inlet holes 58 in communication with the drug reservoir (not shown). The drug formulation passes, under pressure, through both inlet holes but only one metering chamber can align with an inlet hole at any one instant. The drug formulation fills the aligned metering chamber 52 placing surfaces "A" and "B" under pressure from the propellant; because the surface area of "B" is larger than the surface area of "A", the chamber rotates in the direction of "B" (see arrow Z). At this point (not shown), metering chamber 50 fills with drug formulation and metering chamber 52 discharges the drug to the patient.

The metered dose inhalers may be prepared by methods of the art (e.g. see Byron above and U.S. Pat. No. 5,345,980).

Conventionally, the canisters and caps for use in MDI's are made of aluminium or an alloy of aluminium although other metals not affected by the drug formulation, such as stainless steel, an alloy of copper, or tin plate, may be used. An MDI canister may also be fabricated from glass or plastic. Preferably, however, the MDI canisters and caps employed in the present invention are made of aluminium or an alloy thereof.

The drug-metering valve may consist of parts usually made of stainless steel, a pharmacologically resilient polymer, such as acetal, polyamide (e.g. Nylon$^R$), polycarbonate, polyester, fluorocarbon polymer (e.g. Teflon$^R$) or a combination of these materials. Additionally, seals and "O" rings of various materials (e.g., nitrile rubbers, polyurethane, acetyl resin, fluorocarbon polymers), or other elastomeric materials are employed in and around the valve.

The sealing ring may be formed by cutting a ring from a sheet of suitable material. Alternatively, the sealing ring may be formed by a moulding process such as an injection moulding, a compression moulding or a transfer moulding process.

Typically, the sealing ring and/or second sealing ring comprise an elastomeric material. The ring is typically resiliently deformable.

The elastomeric material may either comprise a thermoplastic elastomer (TPE) or a thermoset elastomer which may optionally be cross-linked. The sealing ring may also comprise a thermoplastic elastomer blend or alloy in which an elastomeric material is dispersed in a thermoplastic matrix. The elastomers may optionally additionally contain conventional polymer additives such as processing aids, colorants, tackifiers, lubricants, silica, talc, or processing oils such as mineral oil in suitable amounts.

Suitable thermoset rubbers include butyl rubbers, chlorobutyl rubbers, bromo-butyl rubbers, nitrile rubbers, silicone rubbers, flurosilicone rubbers, fluorocarbon rubbers, polysulphide rubbers, polypropylene oxide rubbers, isoprene rubbers, isoprene-isobutene rubbers, isobutylene rubbers or neoprene (polychloroprene) rubbers.

Suitable thermoplastic elastomers comprise a copolymer of about 80 to about 95 mole percent ethylene and a total of about 5 to about 20 mole percent of one or more comonomers selected from the group consisting of 1-butene, 1-hexene, and 1-octene as known in the art. Two or more such copolymers may be blended together to form a thermoplastic polymer blend.

Another suitable class of thermoplastic elastomers are the styrene-ethylene/butylene-styrene block copolymers. These copolymers may additionally comprise a polyolefin (e.g. polypropylene) and a siloxane.

Thermoplastic elastomeric material may also be selected from one or more of the following: polyester rubbers, polyurethane rubbers, ethylene vinyl acetate rubber, styrene butadiene rubber, copolyether ester TPE, olefinic TPE, polyester amide TPE and polyether amide TPE.

Other suitable elastomers include ethylene propylene diene rubber (EPDM). The EPDM may be present on its own or present as part of a thermoplastic elastomer blend or alloy, e.g. in the form of particles substantially uniformly dispersed in a continuous thermoplastic matrix (e.g. polypropylene or polyethylene). Commercially available thermoplastic elastomer blend and alloys include the SANTOPRENE™ elastomers. Other suitable thermoplastic elastomer blends include butylpolyethylene (e.g. in a ratio ranging between about 2:3 and about 3:2) and butylpolypropylene.

Any parts of the valve that contact the pharmaceutical aerosol suspension may be coated with materials such as fluoropolymer materials which reduce the tendency of medicament to adhere thereto. Suitable fluoropolymers include polytetrafluoroethylene (PTFE) and fluoroethylene propylene (FEP). Any movable parts may also have coatings applied thereto which enhance their desired movement characteristics.

Frictional coatings may therefore be applied to enhance frictional contact and lubricants used to reduce frictional contact as necessary.

Typically, the sealing ring and/or the second sealing ring additionally comprises lubricant material. Suitably, the sealing ring and/or the second sealing ring comprises up to 30%, preferably from 5 to 20% lubricant material.

In addition, the stem may also comprise lubricant material. Suitably, the valve stem comprises up to 30%, preferably from 5 to 20% lubricant material.

The term 'lubricant' herein means any material that reduces friction between the valve stem and seal. Suitable lubricants include silicone oil or a fluorocarbon polymer such as polytetrafluoroethane (PTFE) or fluoroethylene propylene (FEP).

Lubricant can be applied to the stem, sealing ring or a second sealing ring by any suitable process including coating and impregnation, such as by injection or a tamponage process.

In medical use the canisters in accordance with the invention contain a pharmaceutical aerosol formulation comprising a medicament and a fluorocarbon or hydrogen-containing chlorofluorocarbon propellant.

Suitable propellants include, for example, $C_{1-4}$hydrogen-containing chlorofluorocarbons such as $CH_2ClF$, $CClF_2CHClF$, $CF_3CHClF$, $CHF_2CClF_2$, $CHClFCHF_2$, $CF_3CH_2Cl$ and $CClF_2CH_3$; $C_{1-4}$hydrogen-containing fluorocarbons such as $CHF_2CHF_2$, $CF_3CH_2F$, $CHF_2CH_3$ and $CF_3CHFCF_3$; and perfluorocarbons such as $CF_3CF_3$ and $CF_3CF_2CF_3$.

Where mixtures of the fluorocarbons or hydrogen-containing chlorofluorocarbons are employed they may be mixtures of the above identified compounds or mixtures, preferably binary mixtures, with other fluorocarbons or hydrogen-containing chlorofluorocarbons for example $CHClF_2$, $CH_2F_2$ and $CF_3CH_3$. Preferably a single fluorocarbon or hydrogen-containing chlorofluorocarbon is employed as the propellant. Particularly preferred as propellants are $C_{1-4}$hydrogen-containing fluorocarbons such as 1,1,1,2-tetrafluoroethane($CF_3CH_2F$) and 1,1,1,2,3,3,3-heptafluoro-n-propane ($CF_3CHFCF_3$) or mixtures thereof.

The pharmaceutical formulations for use in the canisters of the invention contain no components that provoke the degradation of stratospheric ozone. In particular the formulations are substantially free of chlorofluorocarbons such as $CCl_3F$, $CCl_2F_2$ and $CF_3CCl_3$.

The propellant may additionally contain a volatile adjuvant such as a saturated hydrocarbon for example propane, n-butane, isobutane, pentane and isopentane or a dialkyl ether for example dimethyl ether. In general, up to 50% w/w of the propellant may comprise a volatile hydrocarbon, for example 1 to 30% w/w. However, formulations that are free or substantially free of volatile adjuvants are preferred. In certain cases, it may be desirable to include appropriate amounts of water, which can be advantageous in modifying the dielectric properties of the propellant.

A polar co-solvent such as $C_{2-6}$ aliphatic alcohols and polyols e.g. ethanol, isopropanol and propylene glycol, preferably ethanol, may be included in the drug formulation in the desired amount to improve the dispersion of the formulation, either as the only excipient or in addition to other excipients such as surfactants. Suitably, the drug formulation may contain 0.01 to 5% w/w based on the propellant of a polar co-solvent e.g. ethanol, preferably 0.1 to 5% w/w e.g. about 0.1 to 1% w/w.

A surfactant may also be employed in the aerosol formulation. Examples of conventional surfactants are disclosed in EP 372777. The amount of surfactant employed is desirable in the range 0.0001% to 50% weight to weight ratio relative to the medicament, in particular, 0.05 to 5% weight to weight ratio. Preferred surfactants are lecithin, oleic acid and sorbitan trioleate. Preferred formulations, however, are free or substantially free of surfactant.

Pharmaceutical formulations may contain 0.0001 to 50% w/w, preferably 0.001 to 20%, for example 0.001 to 1% of sugar relative to the total weight of the formulation. Generally the ratio of medicament to sugar falls within the range of 1:0.01 to 1:100 preferably 1:0.1 to 1:10. Typical sugars which may be used in the formulations include, for example, sucrose, lactose and dextrose, preferably lactose, and reducing sugars such as mannitol and sorbitol, and may be in micronised or milled form.

The final aerosol formulation desirably contains 0.005-10% w/w, preferably 0.005 to 5% w/w, especially 0.01 to 1.0% w/w, of medicament relative to the total weight of the formulation.

Medicaments that may be administered in the aerosol formulations include any drug useful in inhalation therapy. Appropriate medicaments may thus be selected from, for example, analgesics, e.g. codeine, dihydromorphine, ergotamine, fentanyl or morphine; anginal preparations, e.g. diltiazem; antiallergics, e.g. cromoglycate, ketotifen or nedocromil; antiinfectives e.g. cephalosporins, penicillins, streptomycin, sulphonamides, tetracyclines and pentamidine; antihistamines, e.g. methapyrilene; anti-inflammatories, e.g. beclomethasone, flunisolide, budesonide, tipredane, triamcinolone acetonide, fluticasone or mometasone; antitussives, e.g. noscapine; bronchodilators, e.g. ephedrine, epinephrine, fenoterol, formoterol, isoprenaline, metaproterenol, phenylephrine, phenylpropanolamine, pirbuterol, reproterol, rimiterol, salbutamol, salmeterol, terbutaline, isoetharine, tulobuterol, orciprenaline, or (−)-4-amino-3,4-dichloro-α-[[[6-[2-(2-pyridinyl)ethoxy]hexyl] amino]methyl]-benzenemethanol diuretics, e.g. amiloride; anticholinergics e.g. ipratropium, atropine or oxitropium; hormones, e.g. cortisone, hydrocortisone or prednisolone; xanthines e.g. aminophylline, choline theophyllinate, lysine theophyllinate or theophylline; and therapeutic proteins and peptides, e.g. insulin or glucagon. It will be clear to a person skilled in the art that, where appropriate, the medicaments may be used in the form of salts (e.g. as alkali metal or amine salts or as acid addition salts) or as esters (e.g. lower alkyl esters) or as solvates (e.g. hydrates) to optimize the activity and/or stability of the medicament and/or to minimize the solubility of the medicament in the propellant. It will further be clear to a person skilled in the art that where appropriate, the medicaments may % be used in the form of a pure isomer, for example, R-salbutamol or RR formotenol.

Particularly preferred medicaments for administration using aerosol formulations in accordance with the invention include anti-allergics, bronchodilators and anti-inflammatory steroids of use in the treatment of respiratory disorders such as asthma by inhalation therapy, for example cromoglycate (e.g. as the sodium salt), salbutamol (e.g. as the free base or the sulphate salt), salmeterol (e.g. as the xinafoate salt), formoterol (e.g. as the fumarate salt), terbutaline (e.g. as the sulphate salt), reproterol (e.g. as the hydrochloride salt), a beclomethasone ester (e.g. the dipropionate), a fluticasone ester (e.g. the propionate). Salmeterol, especially salmeterol xinafoate, salbutamol, fluticasone propionate, beclomethasone dipropionate and physiologically acceptable salts and solvates thereof are especially preferred.

It will be appreciated by those skilled in the art that the aerosol formulations according to the invention may, if desired, contain a combination of two or more active ingredients. Aerosol compositions containing two active ingredients are known for the treatment of respiratory disorders such as asthma, for example, formoterol and budesonide, salmeterol (e.g. as the xinafoate salt) and fluticasone (e.g. as the propionate ester), salbutamol and beclomethasone (as the dipropionate ester) are preferred.

Particularly preferred formulations for use in the canisters of the present invention comprise a medicament and a $C_{1-4}$ hydrofluoroalkane particularly 1,1,1,2-tetrafluoroethane and 1,1,1,2,3,3,3-n-heptafluoropropane or a mixture thereof as propellant.

Preferred formulations are free or substantially free of formulation excipients. Thus, preferred formulations consist essentially of (or consist of) the medicament and the selected propellant.

Conventional bulk manufacturing methods and machinery well known to those skilled in the art of pharmaceutical aerosol manufacture may be employed for the preparation of large scale batches for the commercial production of filled canisters. Thus, for example, in one bulk manufacturing method a metering valve is crimped onto an aluminium can to form an empty canister. The particulate medicament is added to a charge vessel and liquified propellant is pressure filled through the charge vessel into a manufacturing vessel. The drug suspension is mixed before re-circulation to a filling machine and an aliquot of the drug suspension is then filled through the metering valve into the canister. Typically, in batches prepared for pharmaceutical use, each filled canister is check-weighed, coded with a batch number and packed into a tray for storage before release testing.

Each filled canister is conveniently fitted into a suitable channeling device prior to use to form a metered dose inhaler for administration of the medicament into the lungs or nasal cavity of a patient. Suitable channeling devices comprise for example a valve actuator and a cylindrical or cone-like passage through which medicament may be delivered from the filled canister via the metering valve to the nose or mouth of a patient e.g. a mouthpiece actuator. Metered dose inhalers are designed to deliver a fixed unit dosage of medicament per actuation or "puff", for example in the range of 10 to 5000 microgram medicament per puff.

Administration of medicament may be indicated for the treatment of mild, moderate or severe acute or chronic symptoms or for prophylactic treatment. It will be appreciated that the precise dose administered will depend on the age and condition of the patient, the particular particulate medicament used and the frequency of administration and will ultimately be at the discretion of the attendant physician. When combinations of medicaments are employed the dose of each component of the combination will in general be that employed for each component when used alone. Typically, administration may be one or more times, for example from 1 to 8 times per day, giving for example 1,2,3 or 4 puffs each time. Each valve actuation, for example, may deliver 5 μg, 50 μg, 100 μg, 200 μg or 250 μg of a medicament. Typically, each filled canister for use in a metered dose inhaler contains 60, 100, 120 or 200 metered doses or puffs of medicament; the dosage of each medicament is either known or readily ascertainable by those skilled in the art.

A still further aspect of the present invention comprises a method of treating respiratory disorders such as, for example, asthma, which comprises administration by inhalation of an effective amount of an aerosol formulation as herein described from a metered dose inhaler of the present invention.

It is to be understood that the examples given are merely exemplary and that minor modifications may be made thereto without departing from the scope of the invention as set out in the claims.

The invention claimed is:

1. A propellant-operable metering valve for an aerosol container, said metering valve being adapted to dispense a formulation comprising a substance in a fluid propellant contained therein, said metering valve comprising:
   a valve body; and
   a valve member, said valve member being moveable within said valve body; and
   a latch for latching the valve member against movement;
   wherein said valve member includes a first reaction surface and a second reaction surface, and wherein said valve member is, upon release of said latch, movable by pressure exerted by the propellant on said first reaction surface to drive said valve member from a first position to a second position within said valve body, and said valve member is also movable by pressure exerted by the propellant on said second reaction surface to return said valve member to said first position.

2. The metering valve of claim 1, wherein said metering valve is breath-operable.

3. The metering valve of claim 1, wherein said latch is for latching the valve member in its second position on movement thereto from said first position and for latching said valve member in its first position on its return thereto from said second position.

4. The metering valve of claim 3, wherein said latch comprises a lock selected from the group consisting of a mechanical manual-activation lock, an electronic activation lock, an electrically-operated activation lock, a breath-activation lock and combinations thereof.

5. The metering valve of claim 1, wherein said movement of said valve member between said first and second positions switches said metering valve between a first dispensing sequence wherein one dose of formulation is discharged from said metering valve, and a second dispensing sequence wherein a second dose of formulation is dispensed from said metering valve.

6. The metering valve of claim 5, wherein said valve member and said valve body define a first metering chamber having a first metering volume and a second metering chamber having a second metering volume.

7. The metering valve of claim 6, wherein said first metering volume and said second metering volume are substantially equal.

8. The metering valve of claim 6, wherein said valve body has a first priming inlet that allows flow of formulation into said first metering chamber to form said first metering volume and a second priming inlet that allows flow of formulation into said second metering chamber to form said second metering volume.

9. The metering valve of claim 5, wherein said valve member comprises a valve stem and pressure exerted by the propellant elicits a reciprocal piston movement of said valve stem within said valve body to switch said metering valve between said first and said second dispensing sequences.

10. The metering valve of claim 9, wherein said valve stem and said valve body define annular first and second metering chambers.

11. The metering valve of claim 9, wherein said first reaction surface takes the form of a first piston head surface and said second reaction surface takes the form of a second piston head surface.

12. The metering valve of claim 11, wherein said cross-sectional area of said second reaction surface is greater than said cross-sectional area of said first reaction surface.

13. The metering valve of claim 5, wherein said valve member comprises a rotating disk and pressure exerted by the propellant elicits clockwise rotation of said disk within said valve body to switch said metering valve between said first and the second dispensing sequences.

14. The metering valve of claim 13, wherein pressure exerted by the propellant elicits counter-clockwise rotation of said disk within said valve body to drive said metering valve between the first and the second dispensing sequences.

15. The metering valve of claim 13, wherein said rotating disk and said valve body define wedge-shaped annular first and second metering chambers.

16. The metering valve of claim 15, wherein each of said first and second metering chambers have first and second opposing faces defined by said disk, said first face comprising a leading face and said second face comprising a secondary face, said leading face having a greater cross-sectional area than said secondary face, such that said first leading face comprises said first reaction surface and said second leading face comprising said second reaction surface.

17. The metering valve of claim 16, wherein said first and said second reaction surfaces have substantially equal cross-sectional areas.

18. A method for dispensing a formulation, the method comprising:
   providing the formulation having a substance in fluid propellant in a metered dose inhaler having a metering valve, the metering valve comprising a valve member which is movable from a first position to a second position and vice-versa, the metering valve having first and second reaction surfaces, and the metering valve having a latch for latching the valve member against movement, wherein after dispensing one dose the inhaler is automatically primed for further dose release; and
   in a propellant-driven operative cycle, releasing the latch, wherein pressure is exerted by the propellant on the first reaction surface to drive the valve member from the first position to the second position, and pressure is exerted by the propellant on the second reaction surface to return the valve member to the first position.

19. The method of claim 18, wherein said propellant-driven operative cycle comprises a first dispensing sequence and a second dispensing sequence, the first dispensing sequence comprising:
   propellant-driven formation of a first charging first metering chamber;
   the formation of a defined first metering volume;
   a second dispensing position wherein the second metering volume is discharged to the patient; and
   a return to the first charging position.

20. The method of claim 18 wherein the operative cycle comprises the steps of latching the valve member with the latch when the valve member is in both the first and second positions.

21. A metered dose inhaler for dispensing a pharmaceutical formulation, comprising:
a pressurized container, said container having a pharmaceutical formulation and a propellant disposed therein; and
a metering valve having a valve body and a valve member, said valve member being moveable within said valve body, and a latch for latching the valve member against movement, wherein said valve member includes a first reaction surface and a second reaction surface, and wherein said valve member is, upon release of said latch, movable by pressure exerted by the propellant on said first reaction surface to drive said valve member from a first position to a second position within said valve body, and said valve member is also movable by pressure exerted by the propellant on said second reaction surface to return said valve member to said first position.

22. The metered dose inhaler of claim 21, wherein said metering valve is breath-operable.

23. The metered dose inhaler of claim 22, wherein said metering valve comprises a monitor for monitoring the breath cycle of a patient.

24. The metered dose inhaler of claim 23, wherein said monitor comprises at least one sensor for sensing at least one breath profile associated with said breath cycle.

25. The metered dose inhaler of claim 24, wherein said breath profile is selected from the group consisting of a pressure profile, an airflow profile, a temperature profile, a moisture profile and a chemical profile.

26. The metered dose inhaler of claim 24, wherein said monitor provides a signal for dispensing the formulation at a trigger point.

27. The metered dose inhaler of claim 26, wherein said monitor comprises an electronic information process that has a predictive algorithm for predicting the optimal trigger point.

28. The metered dose inhaler of claim 21, wherein said latch is for latching the valve member in its second position on movement thereto from the first position and for latching the valve member in its first position on its return thereto from the second position.

29. The metered dose inhaler of claim 28, wherein said latch comprises a lock selected from the group consisting of a mechanical manual-activation lock, an electronic activation lock, an electrically-operated activation lock, a breath-activation lock and combinations thereof.

30. The metered dose inhaler of claim 21, wherein said movement of said valve member between said first and second positions switches said metering valve between a first dispensing sequence wherein one dose of said pharmaceutical formulation is discharged from said metering valve, and a second dispensing sequence wherein a second dose of said pharmaceutical formulation is dispensed from said metering valve.

31. The metered dose inhaler of claim 30, wherein said valve member and said valve body define a first metering chamber having a first metering volume and a second metering chamber having a second metering volume.

32. The metered dose inhaler of claim 31, wherein said first metering volume and said second metering volume are substantially equal.

33. The metered dose inhaler of claim 31, wherein said valve body has a first priming inlet that allows flow of said pharmaceutical formulation into said first metering chamber to form said first metering volume, and a second priming inlet that allows flow of said pharmaceutical formulation into said second metering chamber to form said second metering volume.

34. The metered dose inhaler of claim 31, wherein said valve member comprises a rotating disk and pressure exerted by said propellant elicits clockwise rotation of said disk within said valve body to switch said metering valve between said first and the second dispensing sequences.

35. The metered dose inhaler of claim 34, wherein pressure exerted by said propellant elicits counter-clockwise rotation of said disk within said valve body to drive said metering valve between said first and the second dispensing sequences.

36. The metered dose inhaler of claim 34, wherein said rotating disk and said valve body define wedge-shaped annular first and second metering chambers.

37. The metered dose inhaler of claim 36, wherein each of said first and second metering chambers have first and second opposing faces defined by said disk, said first face comprising a leading face and said second face comprising a secondary face, said leading face having greater cross-sectional area than said secondary face, such that said first leading face comprises said first reaction surface and said second leading face comprising said second reaction surface.

38. The metered dose inhaler of claim 37, wherein said first and said second reaction surfaces have substantially equal cross-sectional areas.

39. The metered dose inhaler of claim 30, wherein said valve member comprises a valve stem and pressure exerted by said propellant elicits a reciprocal piston movement of said valve stem within said valve body to switch said metering valve between said first and said second dispensing sequences.

40. The metered dose inhaler of claim 39, wherein said valve stem and said valve body define annular first and second metering chambers.

41. The metered dose inhaler of claim 39, wherein said first reaction surface takes the form of a first piston head surface and said second reaction surface takes the form of a reaction surface takes the form of a second piston head surface.

42. The metered dose inhaler of claim 41, wherein said cross-sectional area of said second reaction surface is greater than said cross-sectional area of said first reaction surface.

43. The metered dose inhaler of claim 21, wherein said pharmaceutical formulation includes at least one medicament.

44. The metered dose inhaler of claim 43, wherein said medicament is selected from the group consisting of fluticasone propionate, salbutamol, beclomethasone dipropionate, salmeterol, pharmaceutically acceptable salts, solvates or esters thereof and mixtures thereof.

45. The metered dose inhaler of claim 21, wherein said propellant is selected from the group consisting of liquefied HFA 134a, HFA 227 and mixtures thereof.

46. The metered dose inhaler of claim 45, wherein said propellant is substantially free of adjuvants.

* * * * *